United States Patent [19]

Miller

[11] Patent Number: 4,831,559

[45] Date of Patent: May 16, 1989

[54] METHOD AND APPARATUS FOR PERIODICALLY DETERMINING THE FLASH POINT OF A FLAMMABLE LIQUID

[75] Inventor: Neil C. Miller, Bartlesville, Okla.

[73] Assignee: Phillips Petroleum Company, Bartlesville, Okla.

[21] Appl. No.: 890,217

[22] Filed: Jul. 25, 1986

[51] Int. Cl.[4] .................... G06F 15/46; G01N 25/00; G01M 3/20

[52] U.S. Cl. .................... 364/550; 364/496; 374/8; 73/36; 252/408.1; 436/143

[58] Field of Search .............. 364/550, 551, 496, 497; 374/1, 8, 31, 32; 73/36, 37; 436/143, 8; 252/408.1; 324/468

[56] References Cited

U.S. PATENT DOCUMENTS

| | | | |
|---|---|---|---|
| 3,011,337 | 12/1961 | McGlynn | 73/36 |
| 3,440,863 | 4/1969 | Livingston et al. | 73/36 |
| 3,546,109 | 12/1970 | Woodle | 364/551 X |
| 3,748,894 | 7/1973 | White et al. | 73/36 |
| 3,943,775 | 3/1976 | DeBaun | 73/432 R |
| 4,069,018 | 1/1978 | Karna et al. | 436/143 X |
| 4,092,847 | 6/1978 | Lynch et al. | 73/36 |
| 4,169,016 | 9/1979 | Sequeira et al. | 364/497 X |
| 4,361,810 | 11/1982 | Schlosser | 324/468 |
| 4,370,206 | 1/1983 | Razumney | 204/1 T |
| 4,541,988 | 5/1985 | Tozier et al. | 73/27 R X |
| 4,644,478 | 2/1987 | Stephens et al. | 364/550 |
| 4,684,509 | 8/1987 | Bernath | 324/468 X |
| 4,713,772 | 12/1987 | Carlson | 364/496 |

OTHER PUBLICATIONS

Pippen, D. L., "Techniques for Determination of Flash and Fire Points and Impact Sensitivity of Materials in a Gaseous Oxygen Environment," *Material Res. & Standards*, vol. 11, No. 6, Jun. 1971, pp. 35-43, 52 (cl. 73/36).

Liptak, B. G., *Instrument Engineers' Handbook, Process Measurement*, Chilton Book Company, 1982, pp. 755-759, 853, 854.

Primary Examiner—Parshotam S. Lall
Assistant Examiner—Joseph L. Dixon
Attorney, Agent, or Firm—George E. Bogatie

[57] ABSTRACT

Apparatus for automatically monitoring the flash point of a liquid passing through a conduit which includes a closed equilibrator vessel into which a sample stream of the liquid is confined and volatile vapors therefrom are allowed to saturate air introduced into the vessel, and a combustible gas sensor for measuring the percent lower flammable limit of the resulting gas mixture. The system further includes suitable computing means for automatically calculating the Tag closed cup flash point of the sample liquid based on the temperature of the liquid and on the measured percent lower flammable limit, and controlling the operation of the apparatus. A method of determining the flash point of such a liquid is also disclosed.

14 Claims, 4 Drawing Sheets

METHOD AND APPARATUS FOR PERIODICALLY DETERMINING THE FLASH POINT OF A FLAMMABLE LIQUID

The present invention relates generally to the determination of the flash point of a flammable liquid. In one aspect, the invention relates to apparatus for determining the flash point of a flammable liquid stream. In another aspect, the invention relates to a method of automatically monitoring the flash point of a flammable liquid stream.

In moving products through products pipelines, there is a certain amount of mixing between such products. In the case where gasolines and distillates are pumped adjacently through a pipeline, the distillate is contaminated with gasoline at the interface between the products. When cuts are subsequently made between gasoline and distillates, the amount of gasoline going into oil must be limited to a very small quantity to prevent the flash temperature or flash point of the oil from being lowered to an unacceptable level. There is presently no simple, quick and continuous device for measuring the contamination of distillate with gasoline. It therefore normally occurs that an excessive amount of oil is wasted or directed to "slop" in order to assure that the distillate will be protected from unacceptable contamination by gasolines.

It has been demonstrated that the present lower explosive limit (% LEL) or the percent lower flammable limit (% LFL) of the air and vapors in an enclosed space above the mixture of gasoline and distillates can be directly related to the Tag closed cup (TCC) flash point as determined by ASTM Method D56-70 if the temperature of the mixture is known. As used herein, the terms "lower explosive limit" and "lower flammable limit" are employed interchangeably and both refer to the leanest mixture of gas or vapor in air where, once ignition occurs, the gas or vapor will continue to burn after the source of ignition has been removed. The lower flammable limit is the equivalent of 100 percent lower flammable limit while, for example, 50 percent lower flammable limit refers to a mixture of gas or vapor in air containing 50 percent of the gas or vapor present in the lower flammable limit for the same gas or vapor. The term "flash point", as used herein, means the lowest temperature at which a flammable liquid gives off enough vapors to form a flammable or ignitable mixture with air near the surface of the liquid or within the container used. The present invention provides method and apparatus for the rapid determination of gasolines in distillates by bubbling air through a continuous sample stream taken from a flammable liquid stream pssing through a pipeline or the like and measuring the percent lower explosive limits or the percent lower flammable limits of the effluent from a closed chamber through which the sample stream is passed.

It is an object of the present invention to provide improved apparatus for determining the flash point of a flammable liquid.

Another object of the present invention is to provide an improved method of monitoring the flash point of a flammable liquid.

A further object of the present invention is to provide apparatus for automatically monitoring the flash point of a liquid stream passing through a pipeline or the like which is simple, quick, economical and accurate.

Yet another object of the present invention is to provide a method of monitoring the flash point of a liquid stream passing through a pipeline or the like which is simple, quick, accurate and economical.

Still another object of the present invention is to provide method and apparatus for reducing the amount of oil or distillates which must be discarded due to contamination by adjacent gasolines when being pumped through a pipeline.

Other objects, aspects and advantages of the present invention will be readily apparent to those skilled in the art upon study of the specification and claims and the accompanying drawings in which:

Figure 1:
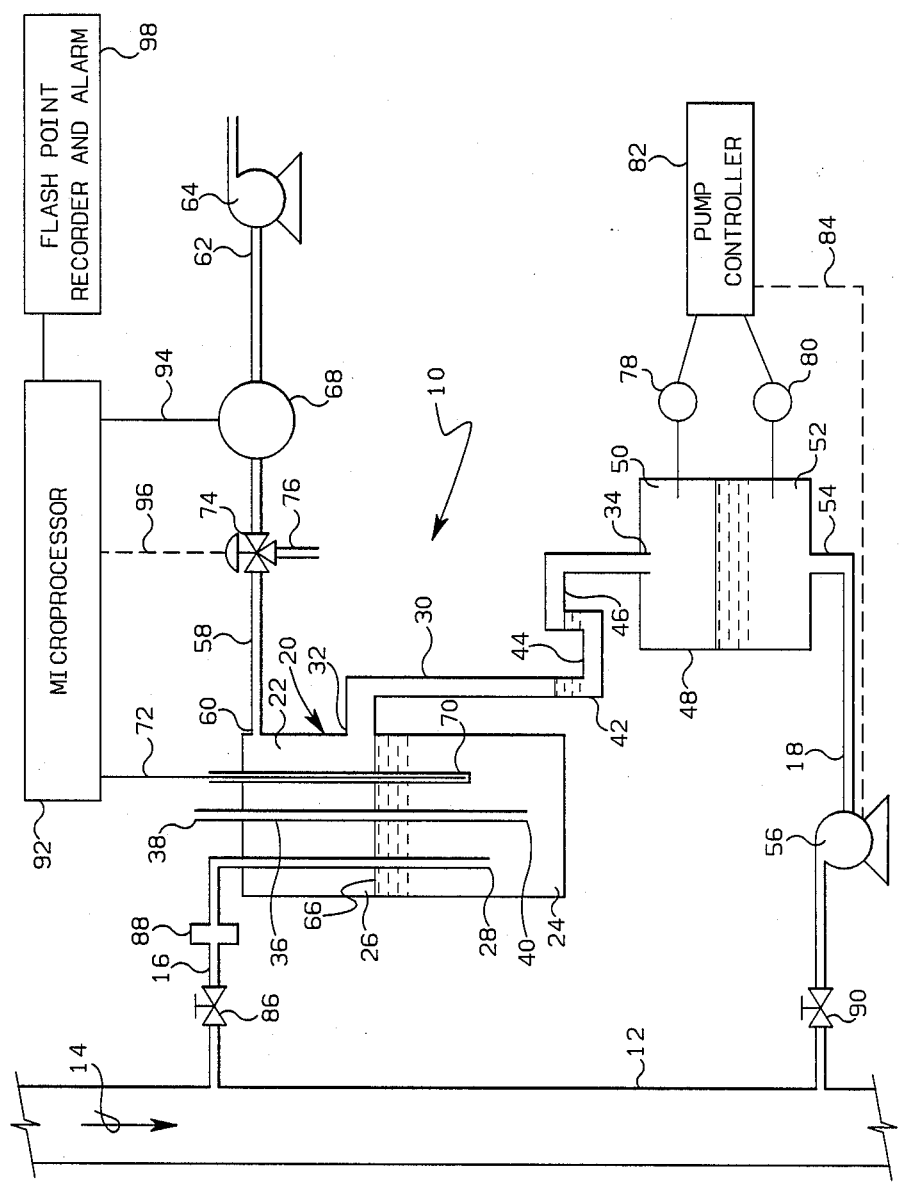
FIG. 1 is a diagrammatic illustration of a system constructed in accordance with the present invention.

Referring now to the drawings, and to FIG. 1 in particular, a flash point monitoring system constructed in accordance with the present invention is generally designated by the reference character 10. The system 10 is illustrated in conjunction with a pipeline 12 through which a stream of flammable liquid is flowing in the direction indicated by the arrow 14. A sample output conduit 16 is connected in fluid flow communication with the pipeline 12. A sample return conduit 18 is also connected in fluid flow communication with the pipeline 12 at a location downstream of the sample output conduit 16. The sample output conduit 16 provides means for withdrawing and passing a stream of sample liquid to the system 10 from the liquid stream passing through the pipeline 12, and the sample return conduit 18 provides means for passing sample liquid back from the system 10 into the liquid stream in the pipeline 12.

The system 10 further includes a closed equilibrator vessel 20 having an upper end portion 22, a lower end portion 24 and a medial portion 26. The interior of the lower end portion 24 of the vessel 20 is in fluid flow communication with the outlet end 28 of the sample output conduit 16 through which sample liquid is introduced into the interior of the vessel 20.

The system 10 is further provided with an equilibrator outlet conduit 30 having an inlet end 32 and an outlet end 34 with the inlet end 32 in fluid flow communication with the interior of the medial portion 26 of the vessel 20 at a location above the outlet end 28 of the sample outlet conduit 16. The equilibrator outlet conduit 30 provides means for passing sample liquid from the equilibrator vessel 20 while retaining a quantity of sample liquid within the lower end portion 24 of the the vessel 20. An oxygen supply conduit 36 having an inlet end 38 and an outlet end 40 is connected in fluid flow communication with the interior of the lower end portion 24 of the equilibrator vessel 20 with the outlet end 40 at a location below the location of fluid flow communication between the equilibrator outlet conduit 30 and the equilibrator vessel 20. The equilibrator outlet conduit 30 is further provided with a liquid trap 42 interposed therein between the inlet end 32 and the outlet end 34. The liquid trap 42 comprises an upwardly opening U-shaped bend 44 formed in the equilibrator outlet conduit 30 and located below and downstream from the inlet end 32 of the conduit 30, and a downwardly opening inverted U-shaped bend 46 formed in the equilibrator outlet conduit 30 located above and downstream from the U-shaped bend 44 and below the inlet end 32 of the conduit 30. The liquid trap 42 provides means for permitting the flow of sample liquid through the equilibrator outlet conduit 30 from the inlet end 32 to the outlet end 34 thereof while blocking passage of gas or vapor through the equilibrator outlet conduit 30.

A surge tank 48, having an upper end portion 50 and a lower end portion 52, is connected to the equilibrator outlet conduit 30 with the outlet end 34 of the conduit 30 in fluid flow communication with the interior of the surge tank 48. The interior of the lower end portion 52 of the surge tank 48 is connected in fluid flow communication with the inlet end 54 of the sample return conduit 18. The surge tank 48 provides means for receiving and accumulating a second quantity of sample liquid therein. The sample return conduit 18 is preferably provided with a suitable pump 56 interposed therein and providing means for pumping sample liquid back to the pipeline 12 via the sample return conduit 18.

A gas sample conduit 58 is connected at its inlet end 60 in fluid flow communication with the interior of the upper end portion 22 of the closed equilibrator vessel 20. The outlet end 62 of the conduit 58 is connected to a suitable vacuum source such as a vacuum pump 64. The vacuum pump 64 provides a means for drawing gas or vapor therethrough from the interior of the closed equilibrator vessel 20 from above the surface 66 of the first quantity of sample liquid retained in the lower end portion 24 of the vessel 20. A combustible gas sensor 68 is interposed in the gas sample conduit 58 intermediate the inlet end 60 and the outlet end 62 thereof. The combustible gas sensor provides means for sensing the percent lower flammable limit of a gas or vapor passing therethrough and providing a percent lower flammable limit signal output representative of the thus sensed percent lower flammable limit. A suitable combustible gas sensor for use in the system 10 is available from Rexnord Gas Detection Products, 207 E. Java Drive, Sunnyvale, Calif. 94086.

A temperature sensor 70 communicates with the interior of the lower end portion 24 of the equilibrator vessel 20 and provides means for sensing the temperature of the first quantity of sample liquid in the lower end portion 24 of the equilibrator vessel 20 and providing a liquid temperature signal output representative of the thus sensed temperature. The temperature sensor 70 is provided with a suitable connecting conduit 72, preferably a 2-wire electrical connecting conduit.

A three-way gas sample valve 74 is interposed in the gas sample conduit 58 intermediate the equilibrator vessel 20 and the combustible gas sensor 68. When the gas sample valve is in its first position, gas or vapor from the equilibrator vessel 20 is free to pass through the gas sample conduit 58, valve 74, combustible gas sensor 68 and vacuum pump 64 thus permitting the combustible gas sensor 68 to analyze or sense the percent lower flammable limit of the gas or vapor from the equilibrator vessel 20. When the gas sample valve 74 is in its second position, gas flow from the equilibrator vessel 20 through the gas sample conduit 58 is blocked by the valve 74 and air from the atmosphere is drawn through inlet port 76, valve 74, combustible gas sensor 68 and gas sample conduit 58 downstream of the valve 74 by means of the vacuum pump 64. By placing the gas sample valve 74 in its second position, the combustible gas sensor 68 can be purged of combustible gases or vapors and its operating life extended by passing atmospheric air therethrough.

A suitable temperature sensor 70 for employment in the system 10 is available from Weed Instrument Co., Inc., 707 Jeffrey Way, Round Rock, Tex. 78664.

The surge tank 48 is provided with an upper liquid level sensor 78 communicating with the interior of the upper end portion 50 thereof and a lower liquid level sensor 80 communicating with the interior of the lower end portion 52 thereof. The upper and lower liquid level sensors 78 and 80 are operatively connected to a suitable pump controller 82 which is, in turn, operatively connected by suitable means 84 to the pump 56. The sensors 78 and 80, pump controller 82 and connecting means 84 provide means for controlling the level of the second quantity of liquid within the surge tank 48. When the upper liquid level sensor 78 detects the level of the second quantity of liquid in the surge tank 48 at a predetermined point in the upper end portion 50 thereof, a first signal output is provided to the pump controller 82 which in turn causes the pump 56 to be activated thus pumping sample liquid from the surge tank 48 to the pipeline 12 via the sample return conduit 18, and when the level of the second quantity of sample liquid in the surge tank 48 reaches a predetermined lower level and the lower end portion 52 thereof, the lower liquid level sensor 80 provides a second signal output to the pump controller 82 which, in turn, deactivates the pump 56 thus stopping the withdrawal of sample liquid from the surge tank 48 by the pump 56.

The sample output conduit 16 is preferably further provided with a shut off valve 86 intermediate the pipeline 12 and the equilibrator vessel 20, and is further preferably provided with a suitable rotameter 88 interposed therein between the valve 86 and the equilibrator vessel 20 to monitor the rate of flow of sample liquid through the sample output conduit 16 when the system 10 is in operation. Similarly, the sample return conduit 18 is preferably provided with a shutoff valve 90 interposed therein intermediate the pipeline 12 and the pump 56. The shutoff valves 86 and 90 provide means for isolating the system 10 from the pipeline 12 when desired.

A suitable computer or microprocessor 92 is operatively connected to the temperature sensor 70 via the connecting conduit 72, to the combustible gas sensor 68 via a suitable electrical conduit 94 and to the 3-way gas sample valve 74 by means of a suitable conduit 96, such as an electrical conduit or a pneumatic conduit, depending on the nature of the actuation device employed with the gas sample valve 74. The microprocessor or computer 92 is further operatively connected to a suitable flash point recorder 98 which may also include therein a visual and/or audible alarm.

Figure 2:
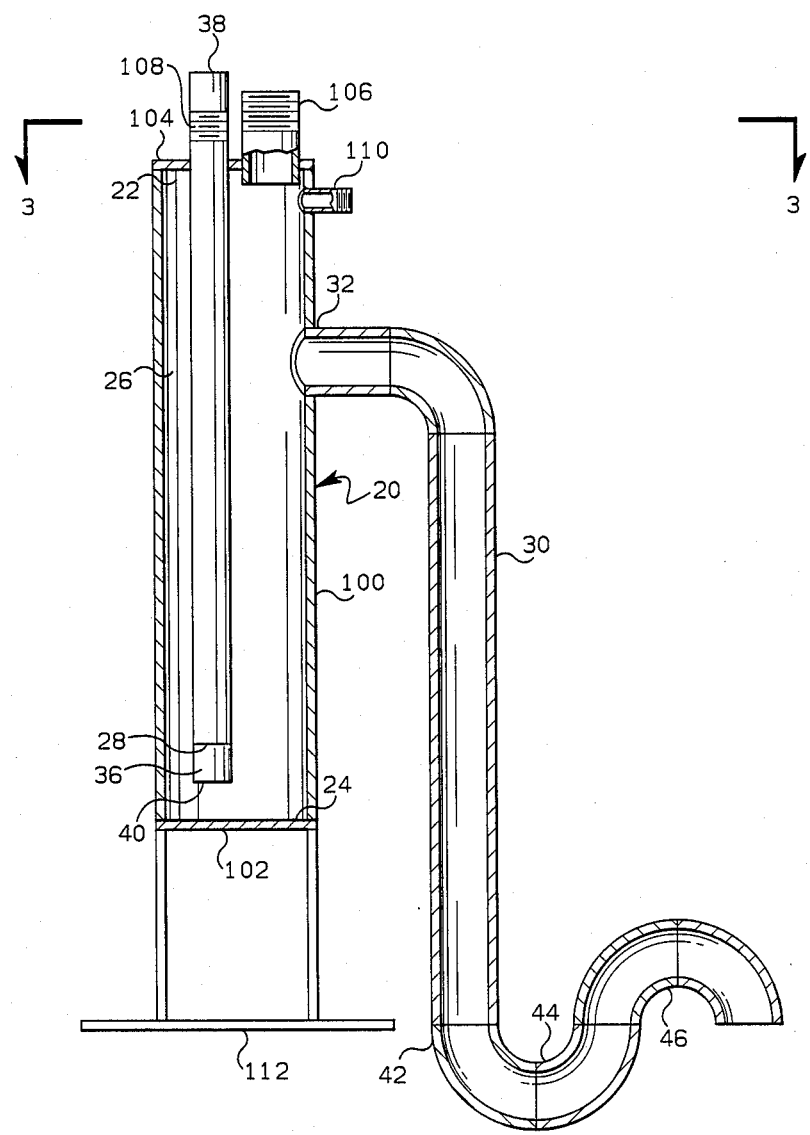
FIG. 2 is a vertical cross-sectional view of a closed equilibrator vessel constructed in accordance with the present invention.
Figure 3:
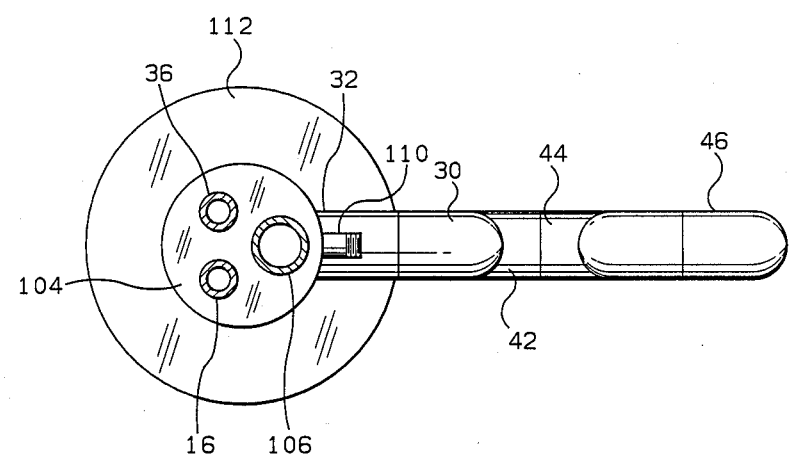
FIG. 3 is a cross-sectional view taken along line 3—3 of FIG. 2.

Referring now to FIGS. 2 and 3, a presently preferred embodiment of the closed equilibrator vessel 20 is illustrated therein. The body of the vessel 20 is preferably constructed of a piece of two inch standard weight pipe 100 having a length of about 8 inches. The lower end portion 24 of the vessel 20 is closed by means of a bottom cap 102 fixedly secured to the lower end portion of the length of pipe 100 by suitable means such as welding or a threaded connection. The upper end portion 22 of the vessel 20 is similarly closed by a suitable top cap 104 secured to the upper end of the two inch pipe 100 by suitable means such as welding or a threaded connection. The top cap 104 is provided with a suitable externally threaded fitting 106 to which the temperature sensor 70 can be threadedly secured with the lower end portion of the temperature sensor 70 extending into the lower end portion 24 of the vessel 20. The top cap 104 is further provided with the terminal end portion of the sample output conduit 16 with the outlet end 28 of the conduit 16 positioned within the lower end portion 24 of the vessel 20. The terminal end portion of the output conduit 16 is provided with an externally threaded portion 108 above the top cap 104 to provide means for connection with the remainder of the sample output conduit 16. Also mounted in the top cap 104 is the oxygen supply conduit 36 with the outlet end 40 thereof located in the lower end portion 24 of the equilibrator vessel 20, and with the inlet end 38 opening to the atmosphere above the top cap 104. An externally threaded fitting 110 is mounted in the upper end portion 22 of the equilibrator vessel 20 and provides means for achieving fluid flow communication between the interior of the upper end portion 22 of the vessel 20 and the inlet end 60 of the gas sample conduit 58.

It is presently preferred that the oxygen supply conduit 36 and the terminal end portion of the sample output conduit 16 each be constructed of ½ inch pipe. The fitting 106 is preferably a ¾ inch externally threaded collar while the fitting 110 is preferably a ¼ inch externally threaded collar. The equilibrator outlet conduit 30 is preferably constructed of 1 inch diameter pipe and ell fittings which can be interconnected by suitable means such as welding, brazing, soldering or threaded connections. The equilibrator vessel 20 is preferably provided with a suitable support base 112 secured to the lower end portion 24 thereof for supporting the vessel 20 in an upright position.

Figure 4:
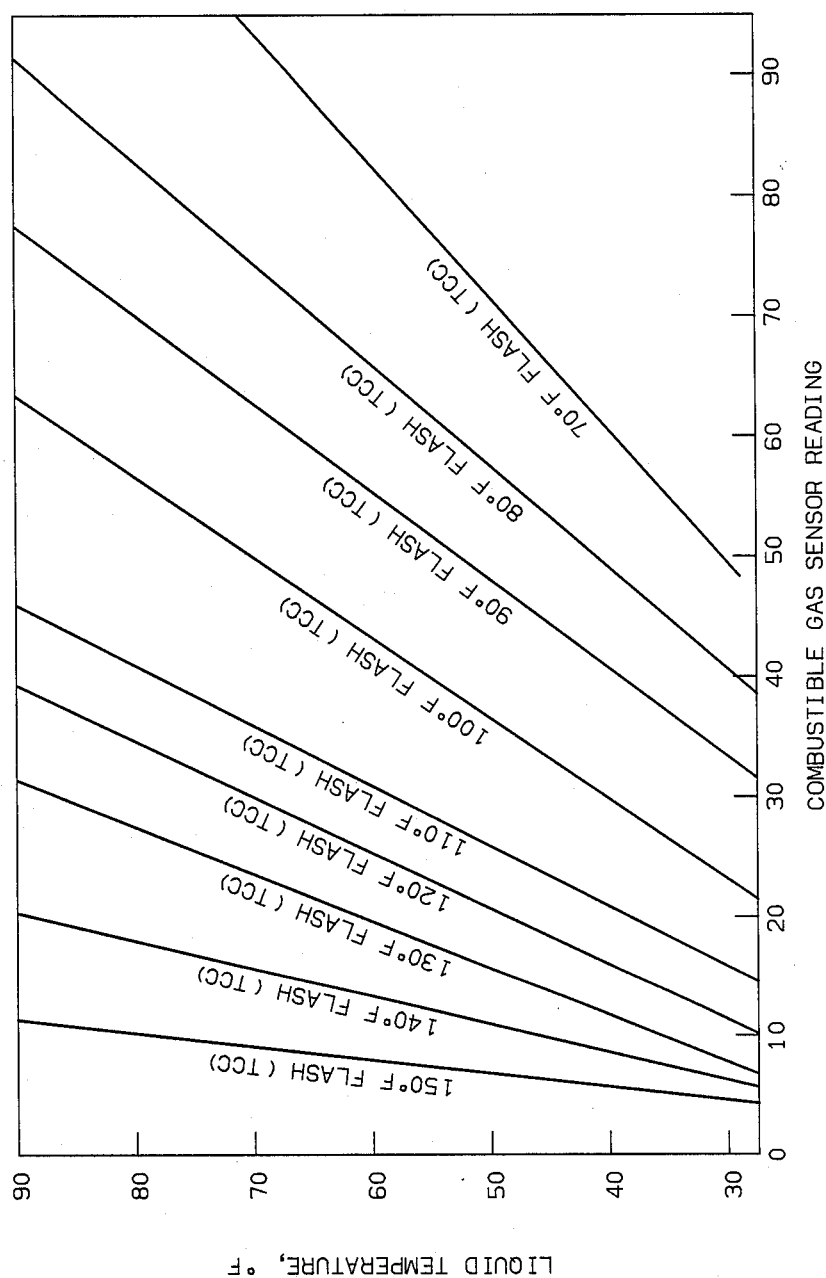
FIG. 4 is a graph illustrating flash points as a function of combustible gas sensor readings and flammable liquid temperature.

In operation, the microprocessor 92, preferably a Siemens-Allis MC-8 Industrial Microcomputer, controls the flashpoint monitoring system 10. With the shutoff valves 86 and 90 in their open position and with the vacuum pump 64 in operation, the microprocesor 92 acting under the control of a suitable program actuates the gas sample valve 74 into its second position placing the combustible gas sensor 68 in communication with atmospheric air. Sample liquid is allowed to pass from the pipeline 12 through the sample output conduit 16 into the equilibrator vessel 20 filling the lower end portion 24 of the vessel 20 with a first quantity of sample liquid to the level of the point of communication between the interior of the medial portion 26 of the vessel 20 and the equilibrator outlet conduit 30. Excess sample liquid passes from the equilibrator vessel 20 through the equilibrator outlet conduit 30 and the liquid trap 42 interposed therein into the surge tank 48 where a second quantity of sample liquid is allowed to accumulate to a level between the upper and lower liquid level sensors 78 and 80. The level in the surge tank 48 is maintained through the action of the level sensors 78 and 80, pump controller 82 and pump 56 in the manner described above. The microprocessor 92 then causes the gas sample valve 74 to be actuated to its first position for a short period of time to allow the vacuum pump to draw air saturated with volatile vapor from the interior of the upper end portion 22 of the vessel 20 through the combustible gas sensor 68 where the percent lower flammable limit of the gas sample is sensed and a signal output representative thereof is directed via conduit 94 to the microprocessor 92. After a sufficient time to obtain a suitable reading from the gas sample by the combustible gas sensor 68, the microprocessor 92 actuates the gas sample valve 74 to its second position for a predetermined period of time whereby the vacuum pump draws atmospheric air through the combustible gas sensor 68 via the control valve 74 to purge the gas sensor and extend its operating life. Simultaneously therewith, the temperature sensor 70 is measuring the temperature of the first quantity of liquid in the equilibrator vessel 20 and is providing a signal output representative thereof via the conduit 72 to the microprocessor 92. The Tag closed cup flashpoint of the sample liquid is then calculated in the microprocessor 92 in response to the signal output from the combustible gas sensor 68 and the signal from the temperature sensor 70 in accordance with known relationships between the percent lower flammable limits and sample liquid temperatures as illustrated in FIG. 4. A signal representative of the calculated flash point is transmitted by the microprocessor 92 to the flash point recorder 98 to provide a permanent record. If the calculated flash point exceeds a predetermined high limit or is below a predetermined low limit, a suitable alarm located at the flash point recorder or other suitable location will be illuminated or sounded. When the alarm condition clears, the visible and/or audible alarms will be reset.

The microprocessor 92 continues to repeat the previously described sequence of steps periodically on a predetermined timed basis. Each calculated flash point is compared in the microprocessor to a specified range of flash points and, if the calculated flash point is within such specified range, the microprocessor sets the system 10 into a "fast cycle" in which the saturated gas from the equilibrator vessel 20 is sampled more frequently than in the standard "slow cycle" mode. The fast cycle and slow cycle delay times can be readily adjusted by an operator of the system 10.

It will be understood that, if desired, the system 10 can be operated manually without the control of the microprocessor 92. Calculations of the flash point of the sample liquid can be manually performed in repsonse to the signal outputs from the combustible gas sensor 68 and the temperature sensor 70 utilizing the same well known relationships therebetween utilized by the microprocessor for calculating the Tag closed cup flash point.

From the foregoing it will be seen that the present invention provides method and apparatus which readily achieve the objects and advantages set forth above. Changes may be made in the combination and arrangement of parts or elements as heretofore set forth in the specification and shown in the drawings without departing from the spirit and scope of the invention as defined in the following claims.

I claim:

1. Apparatus for automatically monitoring the flash point of a liquid stream passing through a pipeline or the like, comprising:

sample output conduit means in fluid flow communication with a pipeline and having an outlet end for passing sample liquid from a liquid stream passing through said pipeline;

sample return conduit means in fluid flow communication with said pipeline downstream of said sample output conduit means for passing sample liquid therethrough, said sample return conduit means having an inlet end;

closed equilibrator vessel means having an upper end portion, a lower end portion and a medial portion, with the interior of the lower end portion thereof being in fluid flow communication with the outlet end of said sample output conduit means for receiving and retaining a first quantity of sample liquid therein;

equilibrator outlet conduit means having an inlet end in fluid flow communication with the interior of the medial portion of said equilibrator vessel means at a location above the outlet end of said sample outlet conduit means, and having an outlet end for passing sample liquid from said equilibrator vessel means therethrough;

oxygen supply conduit means having an inlet end for connection to a source of free oxygen and having an outlet end in fluid flow communication with the interior of the lower end portion of said equilibrator vessel means at a location below the location of fluid flow communication between said equilibrator outlet conduit means and said equilibrator vessel means;

liquid trap means interposed in said equilibrator outlet conduit means for permitting the flow of sample liquid through said outlet conduit means from the inlet end to the outlet end thereof while blocking the passage of gas through said equilibrator outlet conduit means;

surge tank means having an upper end portion and a lower end portion with the interior thereof connected in fluid flow communication with the outlet end of said equilibrator outlet conduit means and with the interior of the lower end portion thereof connected in fluid flow communication with the inlet end of said sample return conduit means for receiving and accumulating a second quantity of sample liquid therein;

gas sample conduit means having an inlet end and an outlet end with the inlet end thereof in fluid flow communication with the interior of the upper end portion of said equilibrator vessel means at a location above the location of fluid flow communication between said equilibrator outlet conduit means and said equilibrator vessel means;

vacuum means connected in fluid flow communication with the outlet end of said gas sample conduit means for drawing gas therethrough from said equilibrator vessel means;

combustible gas sensor means interposed in said gas sample conduit means for sensing the percent lower flammable limit of a gas passing therethrough and providing a percent lower flammable limit signal output representative of said thus sensed percent lower flammable limit;

temperature sensor means communicating with the interior of the lower end portion of said equilibrator vessel means for sensing the temperature of said first quantity of sample liquid in the lower end portion of said equilibrator vessel means and providing a liquid temperature signal output representative of said thus sensed temperature; and flash point determination means connected to said temperature sensor means and said combustible gas sensor means and based on a predetermined relationship between said liquid temperature signal output and said percent lower flammable limit signal output for determining the flash point of said liquid sample passing through said equilibrator vessel means and providing a flash point signal output representative of said thus determined flash point.

2. Apparatus in accordance with claim 1 further comprising:
recorder means connected to said flash point determination means and responsive to said flash point signal output for recording said thus determined flash point.

3. Apparatus in accordance with claim 1 further comprising:
gas sample valve means interposed in said gas sample conduit means intermediate said equilibrator vessel means and said combustible gas sensor means for passing gas therethrough from said equilibrator vessel means to said combustible gas sensor means in a first position of said valve means, and, alternately, for passing air therethrough from the atmosphere to said combustible gas sensor means in a second position of said valve means.

4. Apparatus in accordance with claim 3 wherein said combustible gas sensor means further comprises:
means connected to said gas sample valve means for automatically cycling said sample valve means from the second position to the first position for a first predetermined period of time and back to said first position for a second predetermined period of time and continuing said cycling for an extended period of time to thereby provide automatic periodic determinations of flash point of said gas passing therethrough from said equilibrator vessel means.

5. Apparatus in accordance with claim 1 further comprising:
pump means interposed in said sample return conduit means for pumping sample liquid back to said pipeline.

6. Apparatus in accordance with claim 5 further comprising: means for sensing the level of said second quantity of sample liquid in said surge tank means and providing a first signal output when said level of liquid reaches a predetermined maximum, and, alternately, providing a second signal output when said level of liquid reaches a predetermined minimum; and
pump control means connected to said level control means and responsive to said first and second signal outputs therefrom and operatively connected to said pump means for actuating said pump means in response to said first signal output, and, alternately, for deactivating said pump means in response to said second signal output.

7. Apparatus in accordance with claim 1 further comprising:
first shutoff valve means interposed in said sample output conduit means; and
second shutoff valve means interposed in said sample return conduit means.

8. Apparatus in accordance with claim 1 wherein said source of free oxygen is air and the inlet end of said oxygen supply conduit means is vented to atmosphere.

9. Apparatus in accordance with claim 1 wherein said gas trap means comprises:
and upwardly opening U-shaped bend formed in said equilibrator outlet conduit means located below and downstream from the inlet end thereof; and
a downwardly opening inverted U-shaped bend formed in said equilibrator outlet conduit means located above and downstream from said upwardly opening U-shaped bend and below the inlet end of said equilibrator outlet conduit means.

10. Apparatus in accordance with claim 1 wherein said combustible gas sensor means comprises a catalytic combustion detector.

11. A method of monitoring the flash point of a liquid stream passing through a pipeline or the like, comprising:

(a) withdrawing a sample liquid stream from a liquid stream passing through a pipeline;

(b) introducing said sample liquid stream into a closed vessel having an upper end portion, a lower end portion and a medial portion, and allowing a quantity of said sample liquid to collect in the lower end portion of said vessel;

(c) allowing excess sample liquid to exit said closed vessel via an outlet in the medial portion of said closed vessel;

(d) passing said excess sample liquid through a conduit and liquid trap interposed therein into a surge tank;

(e) withdrawing sample liquid from said surge tank and reintroducing the thus withdrawing sample liquid into said pipeline downstream of the point of withdrawing a sample liquid stream in step (a);

(f) applying a vacuum to the interior of the upper end portion of said closed vessel to draw free oxygen into said quantity of liquid in the lower end portion of said closed vessel below the surface thereof and to draw a vapor stream comprising combustible vapors from said liquid in the lower end portion of said closed vessel and free oxygen from the interior of the upper end portion of said closed vessel;

(e) measuring the temperature of said quantity of liquid in said closed vessel and providing a liquid temperature signal output representative thereof;

(h) measuring the percent lower flammable limit of said vapor stream and providing a percent lower flammable limit signal output representative thereof; and (i) calculating the Tag closed cup flash point of said sample liquid based on a predetermined relationship between said liquid temperature signal output and said percent lower explosive limit signal output.

12. A method in accordance with claim 11 wherein said step (i) is automatically performed by a computer.

13. A method in accordance with claim 11 wherein steps (h) and (i) are performed periodically at predetermined intervals.

14. A method for calculating a flash point for a flammable liquid flowing in a pipeline, wherein said flash point is automatically calculated on-line in an associated computer, said method comprising the steps of:

continuously providing a sample of said flammable liquid to an enclosed space, wherein said enclosed space is attachable to said pipeline;

forming within said enclosed space a zone containing a saturated vapor of said sample of said flammable liquid;

establishing a first signal representative of the lower explosive limit of said saturated vapor;

establishing a second signal representative of the temperature of said flammable liquid in said enclosed space;

predetermining a definite relationship between said flash point of said flammable liquid and said first signal and said second signal;

providing said first signal and said second signal to said computer; and calculating said flash point of said flammable liquid in said computer in accordance with said definite relationship between said flash point of said flammable liquid and said first signal and said second signal.

* * * * *